United States Patent
Sale et al.

(10) Patent No.: US 11,618,760 B2
(45) Date of Patent: Apr. 4, 2023

(54) DIPHOSPHITES WITH AN OPEN, 3-METHYLATED OUTER UNIT

(71) Applicant: EVONIK OPERATIONS GMBH, Essen (DE)

(72) Inventors: Anna Chiara Sale, Recklinghausen (DE); Robert Franke, Marl (DE); Alexander Brächer, Haltern am See (DE); Dirk Fridag, Haltern am See (DE); Ana Markovic, Haltern am See (DE); Peter Kucmierczyk, Herne (DE); Johannes Knossalla, Gahlen (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 17/718,525

(22) Filed: Apr. 12, 2022

(65) Prior Publication Data
US 2022/0332736 A1 Oct. 20, 2022

(30) Foreign Application Priority Data

Apr. 16, 2021 (EP) .................................... 21168825

(51) Int. Cl.
| | | |
|---|---|---|
| C07F 9/6574 | (2006.01) | |
| B01J 31/00 | (2006.01) | |
| C07C 45/00 | (2006.01) | |
| C07F 9/06 | (2006.01) | |

(52) U.S. Cl.
CPC .................................... C07F 9/062 (2013.01)

(58) Field of Classification Search
CPC .. C07F 9/65746; B01J 31/0257; B01J 31/223; C07C 45/50; C07C 45/505
See application file for complete search history.

(56) References Cited

U.S. PATENT DOCUMENTS

2022/0089623 A1   3/2022  Sale et al.

FOREIGN PATENT DOCUMENTS

| | | |
|---|---|---|
| EP | 0 213 639 A2 | 3/1987 |
| EP | 3 763 723 A1 | 1/2021 |

OTHER PUBLICATIONS

R. Franke, et al. "Applied Hydroformylation" Chemical Reviews, 2012, pp. 5675-5732.
U.S. Appl. No. 17/718,542, filed Apr. 2022, Sale et al.
U.S. Appl. No. 17/718,503, filed Apr. 2022, Franke et al.
U.S. Appl. No. 17/696,038, filed Mar. 2022, Sale et al.
European Search Report dated Sep. 2, 2021 for European Patent Application No. 21168825.4 (7 pages in German with English machine translation).

*Primary Examiner* — Sikarl A Witherspoon
(74) *Attorney, Agent, or Firm* — Smith, Gambrell & Russell, LLP

(57) ABSTRACT

Diphosphites having an open, 3-methylated outer unit and use thereof in hydroformylation.

10 Claims, No Drawings

DIPHOSPHITES WITH AN OPEN, 3-METHYLATED OUTER UNIT

The invention relates to diphosphites having an open, 3-methylated outer unit and use thereof in hydroformylation.

Phosphorus-containing compounds play a crucial role as ligands in a multitude of reactions, e.g. in hydrogenation, in hydrocyanation and also in hydroformylation.

The reactions between olefin compounds, carbon monoxide and hydrogen in the presence of a catalyst to afford the aldehydes comprising one more carbon atom are known as hydroformylation or the oxo process. Catalysts used in these reactions are frequently compounds of the transition metals of group VIII of the periodic table of the elements. Known ligands are, for example, compounds from the phosphine, phosphite and phosphonite classes, each containing trivalent phosphorus $P^{III}$. A good overview of the situation on the hydroformylation of olefins can be found in R. Franke, D. Selent, A. Börner, "Applied Hydroformylation", Chem. Rev., 2012, DOI:10.1021/cr3001803.

The following compound is shown in EP 0213639 A2 on page 98 in example 10:

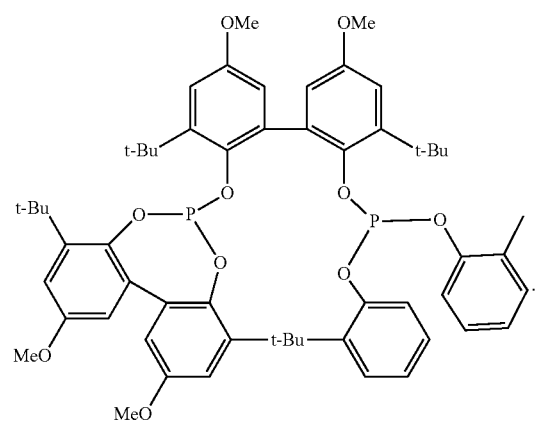

(2)

The compound (2) is used here as ligand in the hydroformylation of 1-butene.

The technical object of the invention is to provide novel ligands that exhibit increased n/iso selectivity in the hydroformylation of olefins compared with the ligand known from the prior art.

The object is achieved by a compound according to Claim 1.

Compound of the structure (I):

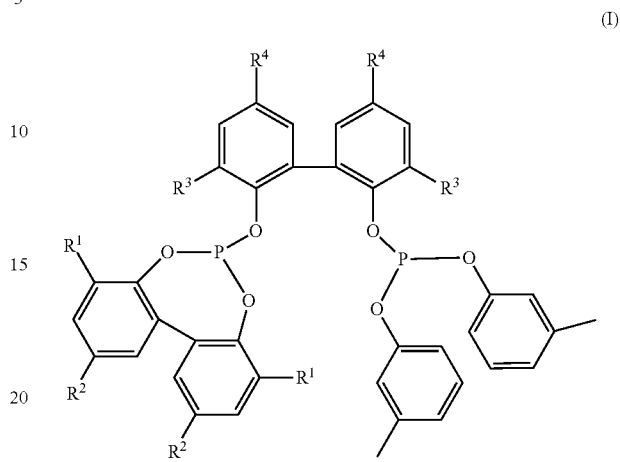

(I)

where $R^1$, $R^2$, $R^3$, $R^4$ are selected from: —H, —($C_1$-$C_{12}$)-alkyl, —O—($C_1$-$C_{12}$)-alkyl.

In one embodiment, $R^1$, $R^3$ are selected from: —H, —($C_1$-$C_{12}$)-alkyl.
In one embodiment, $R^1$, $R^3$ are —($C_1$-$C_{12}$)-alkyl.
In one embodiment, $R^1$, $R^3$ are -tBu.
In one embodiment, $R^1$, $R^3$ are the same radical.
In one embodiment, $R^2$, $R^4$ are selected from: —H, —O—($C_1$-$C_{12}$)-alkyl.
In one embodiment, $R^2$, $R^4$ are —O—($C_1$-$C_{12}$)-alkyl.
In one embodiment, $R^2$, $R^4$ are —OMe.
In one embodiment, $R^2$, $R^4$ are the same radical.
In one embodiment, the compound has the structure (1):

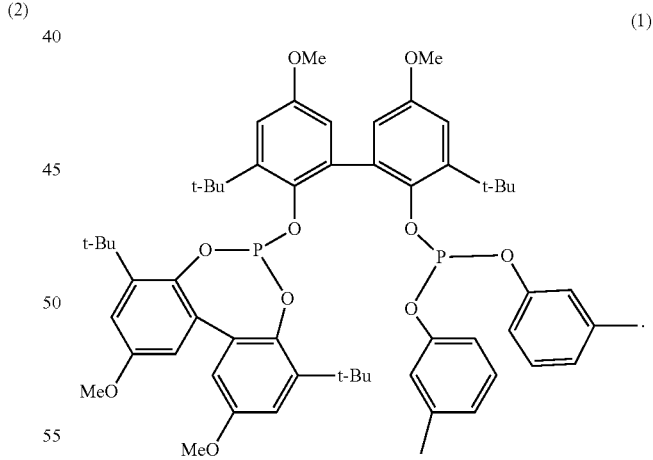

(1)

As well as the compound per se, the use thereof for catalysis of a hydroformylation reaction is also claimed.

Use of a compound described above in a ligand-metal complex for catalysis of a hydroformylation reaction.

Additionally claimed is a process in which the above-described compound is used as a ligand.

Process comprising the process steps of:
a) initially charging an olefin,
b) adding an above-described compound and a substance containing a metal selected from: Rh, Ru, Co, Ir, c) supplying H₂ and CO, d) heating the reaction mixture from steps a) to c), to convert the olefin into an aldehyde.

In a preferred embodiment, the metal is Rh.

The ligands can also be used in excess here and it is not automatically the case that each ligand is present in bound form as a ligand-metal complex; it may instead be present in the reaction mixture as the free ligand.

The reaction is carried out under customary conditions.

Preference is given to a temperature of 80° C. to 160° C. and a pressure of 10 to 60 bar.

Particular preference is given to a temperature of 100° C. to 140° C. and a pressure of 20 to 50 bar.

The reactants for the hydroformylation in the process of the invention are olefins or mixtures of olefins, especially monoolefins having 2 to 24, preferably 3 to 16 and more preferably 3 to 12 carbon atoms, and having terminal or internal C—C double bonds, for example 1-propene, 1-butene, 2-butene, 1- or 2-pentene, 2-methyl-1-butene, 2-methyl-2-butene, 3-methyl-1-butene, 1-, 2- or 3-hexene, the C₆ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl heptene, 2-ethyl-1-hexene, the Ca olefin mixture obtained in the dimerization of butenes (di-n-butene, diisobutene), nonenes, 2- or 3-methyloctenes, the C₉ olefin mixture obtained in the trimerization of propene (tripropene), decenes, 2-ethyl-1-octene, dodecenes, the C₁₂ olefin mixture obtained in the tetramerization of propene or the trimerization of butenes (tetrapropene or tributene), tetradecenes, hexadecenes, the C₁₆ olefin mixture obtained in the tetramerization of butenes (tetrabutene), and olefin mixtures produced by cooligomerization of olefins having different numbers of carbon atoms (preferably 2 to 4).

The process of the invention using the ligands of the invention can be used for the hydroformylation of α-olefins, terminally branched, internal and internally branched olefins.

The invention shall be elucidated in more detail hereinbelow with reference to working examples.

Operating Procedures

General Analysis

All the preparations that follow were carried out under inert gas using standard Schlenk techniques. The solvents were dried before use over suitable drying agents.

The products were characterized by NMR spectroscopy. Chemical shifts (δ) are reported in ppm. The ³¹P NMR signals were referenced as follows: SR³¹P=SR¹H*(BF³¹P/BF¹H)=SR¹H*0.4048.

Synthesis (1)

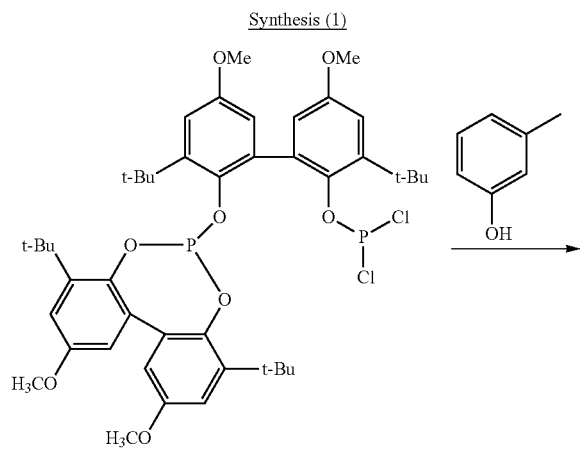

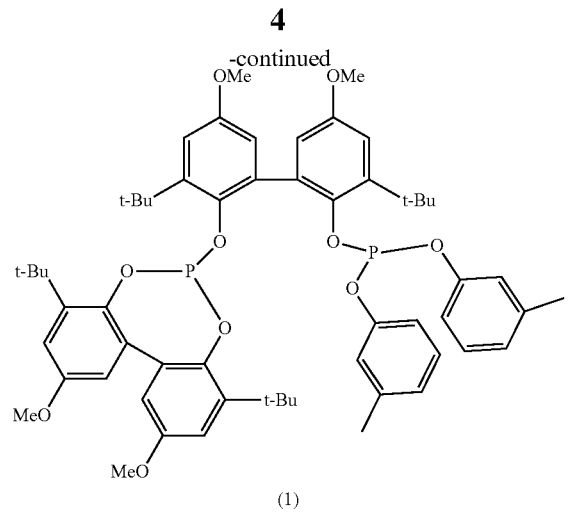

(1)

In a glovebox, 9 g (0.01 mol) of diorganophosphite dichlorophosphite was weighed into a 250 ml Schlenk flask that had been repeatedly filled and evacuated with inert gas, then discharged and dissolved in 75 ml of dried toluene. In a second 250 ml Schlenk flask that had been repeatedly filled and evacuated with inert gas, 2.2 g (2.1 ml, 0.02 mol) of 3-methylphenol was weighed out and dried at room temperature for 12 hours by means of oil-pump vacuum. 50 ml of dried toluene and 3 ml=2.2 g (0.022 mol) of degassed triethylamine were added while stirring and the solids were dissolved. The dichlorophosphite was added at room temperature to the phenol-triethylamine solution over 1.5 h. The reaction was stirred at room temperature for 15 h, and 1.5 ml (0.011 mol) of triethylamine was added. The reaction mixture was then stirred at 80° C. for another 1.5 h. After cooling to room temperature, the ammonium hydrochloride solids were filtered off using a frit, and the filtrate was concentrated by means of oil-pump vacuum at 40° C. The solids obtained were dried further at room temperature by means of oil-pump vacuum for 15 h. Yield: 76%, purity: 90%.

Synthesis (2) (Comparative Ligand)

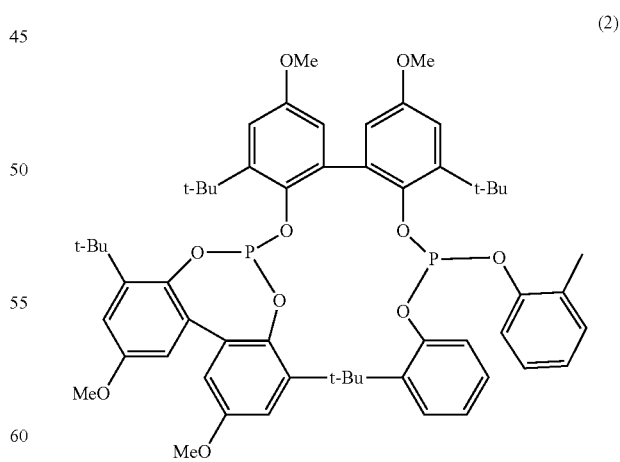

(2)

In a glovebox, 9 g (0.01 mol) of diorganophosphite dichlorophosphite was weighed into a 250 ml Schlenk flask that had been repeatedly filled and evacuated with inert gas, then discharged and dissolved in 75 ml of dried toluene. In a second 250 ml Schlenk flask that had been repeatedly filled and evacuated with inert gas, 2.2 g (2.1 ml, 0.02 mol) of 2-methylphenol was weighed out and dried at room temperature for 12 hours by means of oil-pump vacuum. 50 ml of dried toluene and 3 ml=2.2 g (0.022 mol) of degassed triethylamine were added while stirring and the solids were dissolved. The dichlorophosphite was added at room temperature to the phenol-triethylamine solution over 1.5 hours. The reaction mixture was stirred at room temperature for 2 hours and then heated to 80° C. The reaction mixture was stirred at that temperature for 15 hours, and then there were 3 cycles of metered addition of a further 1.5 ml (0.011 mol) of triethylamine and stirring for a further 15 hours. The ammonium hydrochloride was removed by frit, washed with 1×10 ml of dried toluene and concentrated to dryness. The solids were dried at room temperature for 15 hours and stirred with 40 ml of degassed acetonitrile. The precipitated white solids were removed by frit, the Schlenk flask was rinsed through with 2 lots of 10 ml of ACN, dried and then introduced into a glove box. Yield 90%, purity: 95%.

CATALYSIS EXPERIMENTS

The hydroformylation was carried out in a 16 ml autoclave from HEL Group, Hertfordshire, Great Britain, equipped with a pressure-retaining valve, gas flowmeter and sparging stirrer. The n-octene used as substrate (Oxeno GmbH, mixture of octene isomers composed of 1-octene: 3%; cis+trans-2-octene: 49%; cis+trans-3-octene: 29%; cis+trans-4-octene: 16%; structurally isomeric octenes: 3%) was heated under reflux over sodium for several hours and distilled under argon.

The reaction solutions for the experiments were prepared beforehand under an argon atmosphere. For this, 0.0021 g of $Rh(acac)(CO)_2$ and the corresponding amount of phosphite compound were weighed out and filled with 8.0 ml of toluene. The mass of toluene introduced in each case was determined for the GC analysis. 1.80 g of n-octene (16 mmol) was then added. The prepared solutions were then introduced into the autoclave, which was flushed three times with argon and three times with syngas (Linde; $H_2$ (99.999%):CO (99.997%)=1:1). The autoclave was then heated to the desired temperature at an overall pressure of 10 bar with stirring (900 rpm). On reaching the reaction temperature, the syngas pressure was increased to 20 bar and the reaction carried out at constant pressure for 4 h. At the end of the reaction time, the autoclave was cooled to room temperature, depressurized while stirring and flushed with argon. 0.5 ml of each reaction mixture was removed at the end of the reaction, diluted with 4 ml of pentane and analysed by gas chromatography: HP 5890 Series II plus, PONA, 50 m×0.2 mm×0.5 μm. Residual olefin and aldehyde were quantitatively determined against the solvent toluene as internal standard.

Results of the Catalysis Experiments
Reaction Conditions:
[Rh]: 120 ppm, L:Rh=1:2, p: 20 bar, T: 120° C.; t: 4 h

TABLE 1

| Hydroformylation of n-octenes | |
|---|---|
| Ligand | n/iso selectivity in % |
| 1* | 77 |
| 2 | 56 |

*inventive compound

Definition of Selectivity:

In the hydroformylation there is n/iso selectivity, which is the ratio of linear aldehyde (=n) to branched aldehyde (=iso). The selectivity here in respect of the n-aldehyde signifies that this amount of linear product was formed. The remaining percentages then correspond to the branched isomer. Thus, at a regioselectivity of 50%, n-aldehyde and iso-aldehyde are formed in equal proportions.

The compound of the invention (1) achieved an increase in n/iso selectivity compared with the comparative ligand (2).

The experiments carried out demonstrate that the stated object is achieved by the compound of the invention.

The invention claimed is:
1. A compound of the structure (I):

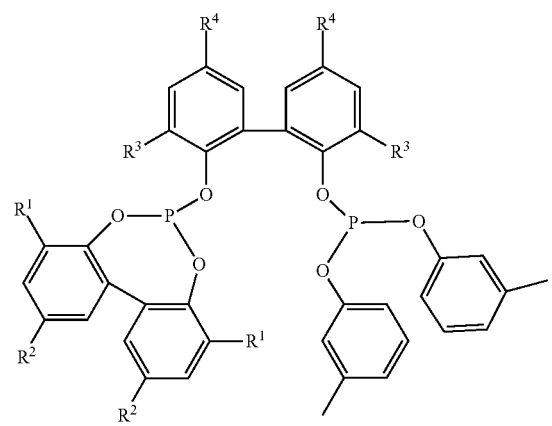

(I)

where $R^1$, $R^2$, $R^3$, $R^4$ are selected from: —H, —($C_1$-$C_{12}$)-alkyl, —O—($C_1$-$C_{12}$)-alkyl.

2. The compound according to claim 1,
wherein $R^1$, $R^3$ are selected from: —H, —($C_1$-$C_{12}$)-alkyl.

3. The compound according to claim 1,
where $R^3$ are —($C_1$-$C_{12}$)-alkyl.

4. The compound according to claim 1,
where $R^1$, $R^3$ are the same radical.

5. The compound according to claim 1,
wherein $R^2$, $R^4$ are selected from: —H, —O—($C_1$-$C_{12}$)-alkyl.

6. The compound according to claim 1,
wherein $R^2$, $R^4$ are —O—($C_1$-$C_{12}$)-alkyl.

7. The compound according to claim 1,
where $R^2$, $R^4$ are the same radical.

8. The compound according to claim 1, where the compound has the structure (1):

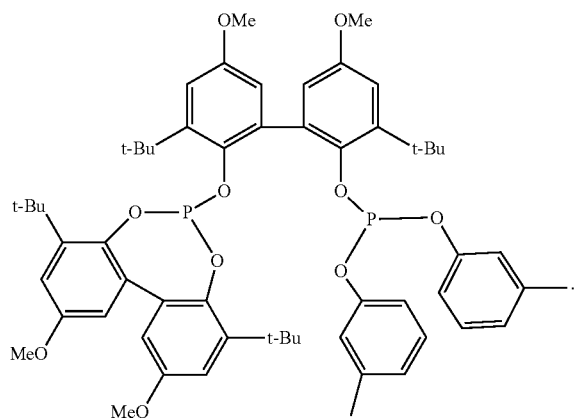

(1)

9. A ligand-metal complex comprising the compound according to claim 1 and a metal selected from: Rh, Ru, Co or Ir.

10. A process comprising the process steps of:
a) initially charging an olefin,
b) adding a compound according to claim 1 and a substance containing a metal selected from: Rh, Ru, Co or Ir,
c) supplying $H_2$ and CO, and
d) heating the reaction mixture from steps a) to c), to convert the olefin into an aldehyde.

* * * * *